United States Patent [19]

Herrick

[11] Patent Number: 4,461,295

[45] Date of Patent: Jul. 24, 1984

[54] LASER PUNCTAL OCCLUSION

[76] Inventor: Robert S. Herrick, 1300 N. Vermont Ave., Suite 401, Los Angeles, Calif. 90027

[21] Appl. No.: 544,283

[22] Filed: Oct. 21, 1983

[51] Int. Cl.³ .................. A61B 3/10; A61B 17/36
[52] U.S. Cl. ................................................ 128/303.1
[58] Field of Search .................. 128/1 R, 303.1; 604/893

[56] References Cited

U.S. PATENT DOCUMENTS

| | | | |
|---|---|---|---|
| 3,949,750 | 4/1976 | Freeman | 604/893 |
| 4,141,362 | 2/1979 | Wurster | 128/303.1 |
| 4,165,744 | 8/1979 | Cravy et al. | 128/303.1 |
| 4,326,529 | 4/1982 | Doss et al. | 128/303.1 |
| 4,391,275 | 7/1983 | Farkhauser et al. | 128/303.1 |

FOREIGN PATENT DOCUMENTS 581941  11/1977  U.S.S.R. ........................... 128/303.1

Primary Examiner—Edward M. Coven
Attorney, Agent, or Firm—Wm. Jacquet Gribble

[57] ABSTRACT

A method for treating external eye conditions and nasal related physical conditions by closing or partially closing one or more eyelid punctal openings by first testing the efficacy of occlusion by a temporary test stitch to close a punctal canaliculus and observe the effect of such enforced retention within the eye of continuous tears that otherwise drain from the eye through the nasolacrimal duct, and then closing or occluding one or more of the lower and upper punctal canaliculi by applying a laser beam to the puntum in phases of differing intensity and diffusion to shrink the epithelium and other tissue in the area to restrict the canaliculus opening.

7 Claims, 4 Drawing Figures

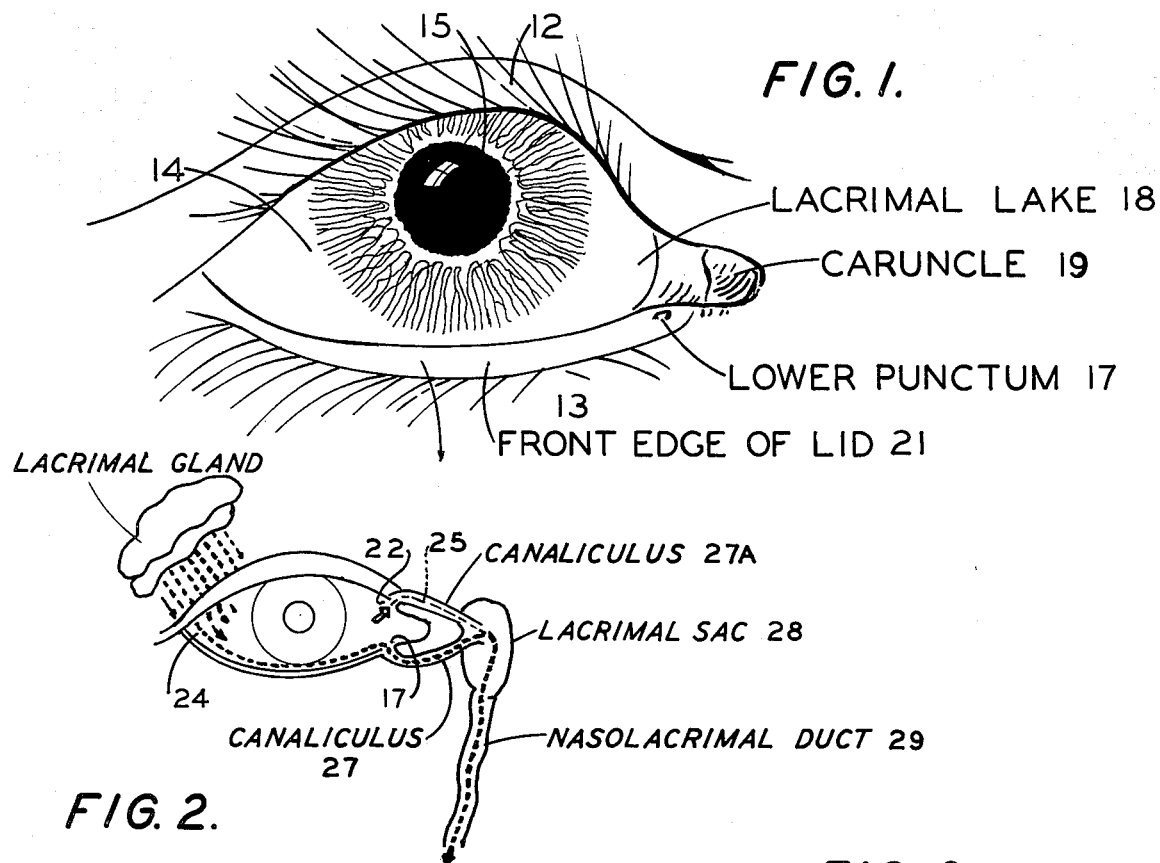
FIG. 1.
FIG. 2.
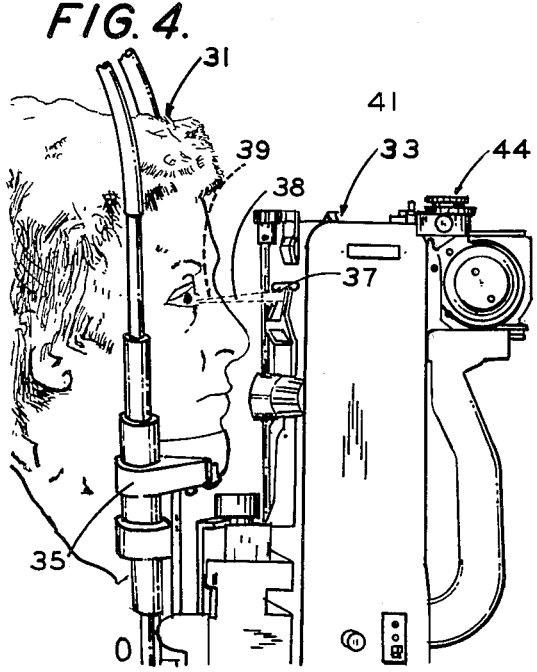
FIG. 4.
FIG. 3.
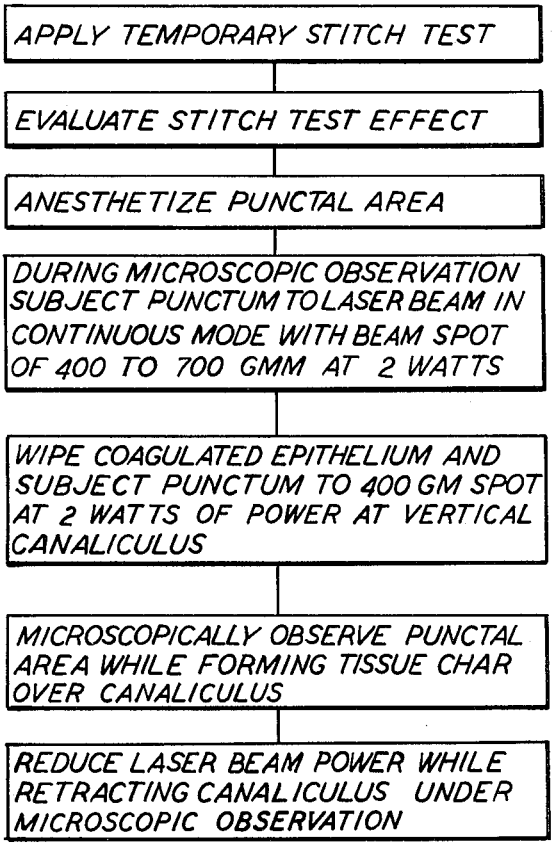

LASER PUNCTAL OCCLUSION

BACKGROUND OF THE INVENTION

The human eye is protected by two types of tears—constant tears from the small glands of Krause and Wolfring in the upper eyelid containing lysozyme and other components, and reflex tears from the main lacrimal gland, that are basically saline. The constant tears are multi-layered to fulfill their lubricating and sanitizing functions while the reflex tears wash or flood the eye to cleanse away foreign objects and additionally provide emotional relief.

Many people suffer from what is called "dry eye", a condition wherein the eye evidences such conditions an conjunctivitis, corneal ulcers, recurrent chalazion, pterygium, chronic blepharitis and problems stemming from wearing soft contact lenses. Dry eye, or kerato-conjunctivitis sicca, has also been discovered to be a factor in recurrent colds, sinus problems and hay fever symptoms because of the close association of the punctum canaliculi and the fluid systems involved in the recited problems.

The work of Tuberville, Fredrick and Wood was reported in 1981 and their reports, relating the results of punctal occlusion by cauterization were positive, but eight of the thirty two cauterized reopened within a short while after the occlusion treatment. This factor discouraged professional followup on the procedure.

Surgical closing of the punctum with fine sutures also proved to be a temporary measure, the stitches being absorbed in seven or eight days after surgery. It was also found that cauterization often enlarged the canaliculus opening after the initial treatment, causing not a retraction of the tissues around the punctal opening but actual increase in opening size due to the destruction of surrounding tissue during cautery. Thus, the failure rate for the intended permanent occlusion was very high.

I have discovered that whole or partial occlusion of the upper and lower punctum has direct bearing on the external eye conditions set forth above, as well as upon the symptomatic involvement of associated areas such as sinus passages, nasal passages and inner ear. By employing a temporary stitch test, not as a traditional treatment, but as a diagnostic step, and employing the energy of a laser beam in controlled phases upon the tissue in the punctal area, I am able to achieve desired occlusion of the punctum that is not only of desired permanence but which may be reversed if necessary.

BRIEF STATEMENT OF THE INVENTION

The invention contemplates a process for treating medically external eye and naso-sinus conditions by punctal occlusion by applying laser beam energy to the punctal area and including the steps of first applying a local anesthetic to the area of the puctum and closing the punctum with a temporary surgical stitch to retain constant tears in the eye, as in the lacrimal lake. Then the eye's response to the closure or occlusion of the punctum is observed. Following the prescribed delay, a second local anesthetic is applied to the punctal area and that area is subjected to a laser beam in the continuous or "paint" mode while the eye is being microscopically observed. The exposed area is from approximately 400 GMM to 700 GMM. The area of the exposure is then reduced in size after the coagulated epithelium tissue at the punctum is wiped away. A second phase includes concentrating a laser beam directly on the vertical canaliculus to contract the punctum tissue as microscopic observation of the tissue char buildup over the canaliculus continues. Laser power is then reduced and continuous application to the punctum area proceeds until complete retraction of the canaliculus is observed.

An alternate method includes the stitch test and anesthetizing but limits the laser beam application to a continuous "paint" mode (wide diffusion) until a desired degree of restriction of the punctum is observed.

The processes stated above may be applied to one or more of the four punctum of a patient's eyes in accordance with the perceived need to preserve constant tears in the eye and bar them from the nasolacrimal channels and ducts. Whole or partial occlusion may be indicated.

While a Britt Argon laser generator is the preferred apparatus other comparable energy sources may be employed. With the Britt machine proper treatment may be achieved with an initial power setting of two watts, which is usually reduced in the later phase of treatment. Where only partial occlusion is desired a first phase in the "paint" mode may be used without a second phase with a more focussed beam.

The process may be practiced in a physician's office in a matter of minutes once the initial data from the temporary stitch test has been evaluated. Since there is needed only a local anesthetic the patient may resume normal activities immediately, with a slightly discolored eye after the stitch test, and local inflamation of the lid from the anesthetic the only outward indications of treatment.

These and other advantages of the inventive method are apparent from the following detailed description and drawing.

DETAILED DESCRIPTION OF THE DRAWING

FIG. 1 is an illustration in front elevation of an eye with the lower lid pulled down to show the punctum;

FIG. 2 is a schematic view of the lacrimal system of an eye;

FIG. 3 is a diagram of the steps of a preferred method of the invention; and

FIG. 4 is a side elevational view of a patient under treatment with a laser beam generator and microscope.

DESCRIPTION OF THE PREFERRED EMBODIMENTS

In FIG. 1 an eye 11 has an upper lid 12 and a lower lid 13 about a cornea 14 and a pupil 15. A punctum 17 in the lower lid is seen adjacent a lacrimal lake 18 and a caruncle 19. A front edge 21 of the lower lid is pulled down so that the punctum is evident. Since the upper lid is not raised or rolled back the upper punctum 22 is shown schematically in FIG. 2. Therefore, both upper and lower punctum are adjacent the fleshy caruncle at the bridge of the nose.

In FIG. 2 the flow of tears from the lacrimal gland is evidenced by heavy dashes 24, with the major flow being through the lower punctum 17 and the minor flow of tears being through the upper punctum 22, shown by the light dashes 25. A canaliculus 27, 27 A leads from each punctum to a lacrimal sac 28 from which a nasolacrimal duct 29 connects to the nasal passages (not shown). It has been thought that the canaliculi acted as passive drains but present views hold the punctum to be active pumps inducing tear flow from the region of the lacrimal lake 18 to the lacrimal sac. Therefore, complete occlusion of one or more canaliculi may be needed to effect a cure of the dry eye condition.

In FIG. 3 a diagram sets forth the steps of a preferred method of practicing the invention, starting with the temporary stitch test. It is usually best to anesthetize the punctum 17 before applying the stitch. A suture like 10-0 nylon is preferred. Citanest 4% ASTRA has proved to be an effective anesthetic with little sting.

Eye conditions were observed to improve the next day in some cases and within the span of from seven to ten days during which the stitch kept the eye canaliculus closed a determination is made as to the value of the treatment for the particular patient. An appointment in the physician's office is then made and local anesthetic again applied to the punctal area.

The patient is seated at the slit lamp of an Argon laser such as a Britt Model 152. The doctor views the eye structures and canaliculus through the slit lamp microscope mounted on the laser generator. An aiming beam is used to target the tissue areas for treatment. A 400 micron spot size with a 1.5 to 2.0 watt setting is used in the first phase of treatment. The laser beam is aimed down the canaliculus and the surrounding tissues with the laser in the continuous mode, or "paint" mode. Laser treatment is applied until a char is built up and the tissues are contracted. Epithelium and mucous material is removed using a cotton "Q-Tip". If a char has not been produced the laser beam may be set at a 200 micron spot size and treatment continued. Then the laser beam is adjusted to a 400 micron spot size at a power setting of from 0.25 to 0.50 watt, for a period of 15 to 20 seconds to obtain additional tissue contraction of the canaliculus and surrounding tissue, while the physician carefully observes the procedure by means of the slit microscope.

Both the horizontal and vertical portions of the canaliculus are treated. A retraction of tissue on the inner aspect of the vertical canaliculus is obtained.

FIG. 4. illustrates a typical office arrangement for practicing the method of the invention, with a patient 31 seated on front of a laser generator such as the Britt Argon laser 33. A chin support 35 under the control of the physician fixes the patient with respect to the emergence slit 37 of the laser beam 38 represented by the broken lines 39 of FIG. 4. The physician observes the punctal area by means of the built-in slit microscope portion 41 while adjusting controls 44 to regulate spot size and power.

While the preferred methods of practicing the invention have been set forth herein, other procedures within the scope of the invention will occur to those skilled in this particular art. Therefore it is desired that the invention be measured by the appended claims rather than by the illustrative specifics set forth herein.

I claim:

1. A method for treating external eye conditions due to a deficiency of retained constant tears by punctal occlusion to at least partially restrict the canaliculus including the steps of applying a local anesthetic to a punctal region of an eye to be treated, stitching the punctum at least partially closed with a temporary surgical suture, observing the response of the eye condition to the closure of punctum, applying a second local anesthetic to the punctal area to be treated, subjecting the punctal area to a laser beam in a diffused pattern until the canaliculus tissue restricts the opening, and cleansing damaged tissue from the punctal area.

2. A method in accordance with claim 1 including the further step of employing a microscope for inspection of the punctum before, during and after subjecting the punctal area to the laser beam.

3. A method in accordance with claim 2 wherein the punctum is subjected to a laser beam in the continuous mode setting at two watts of power and a spot size of from 400 GMM to 700 GMM approximately, measured at the epithelium of the punctum, wiping the coagulated epithelium away, applying an approximately 400 GMM spot beam at two watts of power directly to the vertical canaliculus to contract the punctum tissue, observing the formation of tissue char over the canaliculus, and then reducing the power setting while continuing application of the laser beam until retraction of the canaliculus opening is observed.

4. A method in accordance with claim 3 including applying a laser beam to each of a patient's punctal areas in turn.

5. A method for treating external eye conditions and nasal conditions by punctal occlusion to restrict the canaliculus opening of the eye in order to retain constant tears in the region of the lacrimal lake and other eye areas including the steps of applying a local anesthetic to the punctal region of an eye, stitching closed the punctum with a temporary surgical suture, observing the response of the eye condition to the temporary closure of the punctum, applying a second local anesthetic to the punctal area to be treated, subjecting the punctal area while under microscopic observation to a laser beam of the Argon type in three distinct phases, the first phase being subjecting the punctum to a beam in the continuous mode with the beam set at approximately two watts of power in a spot size of from 400 GMM to 700 GMM, approximately, as measured at the epithelium of the punctum and wiping away the resulting coagulated epithelium tissue; secondly, applying a laser beam in the range of 400 GGM at two watts approximately of power directly to the vertical canaliculus to contract the punctum tissue and observing microscopically the formation of tissue char over the canaliculus; and, thirdly, reducing the laser beam power setting below two watts while continuing the application of the laser beam until retraction of the canaliculus opening is observed.

6. A method in accordance with claim 5 including the steps of applying a laser beam to each of a patient's punctal areas in turn.

7. A method for treating external eye and nasal conditions due to a deficiency of retained constant tears by punctal occlusion and including the steps of applying a local anesthetic to a punctal region of an eye to be treated, stitching the punctum closed with a temporary surgical suture, observing the response of the eye and nasal condition to the closure of the punctum, applying a second local anesthetic to the lower and upper punctum of each eye of the patient, applying to each canaliculus opening a laser beam in the continuous mode, observing microscopically the response of the canaliculus epithelium to the laser beam, and terminating the laser beam upon observing contraction of the canalicular tissue to narrow the opening without charring said tissue.

* * * * *